United States Patent [19]
Johnson Prillerman

[11] Patent Number: 5,958,418
[45] Date of Patent: Sep. 28, 1999

[54] EXTERNAL HERBAL COMPOSITION FOR TREATING MUSCLE ACHES AND JOINT PAIN

[76] Inventor: Kathleen O. Johnson Prillerman, 1341 N. 58th St., Philadelphia, Pa. 19131

[21] Appl. No.: 08/786,529

[22] Filed: Jan. 22, 1997

[51] Int. Cl.⁶ .............................. A61K 35/78; A61K 9/00
[52] U.S. Cl. ...................... 424/195.1; 424/400; 514/825; 514/906; 514/969
[58] Field of Search ................................. 424/195.1, 400; 514/825, 906, 969

[56] References Cited

U.S. PATENT DOCUMENTS

| | | | |
|---|---|---|---|
| 4,719,111 | 1/1988 | Wilson | 424/195.1 |
| 5,215,759 | 6/1993 | Mausner | 424/489 |
| 5,248,503 | 9/1993 | Emanuel-King | 424/195.1 |

FOREIGN PATENT DOCUMENTS

| | | |
|---|---|---|
| 358055427 | 4/1983 | Japan . |
| 402207023 | 8/1990 | Japan . |

*Primary Examiner*—Leon B. Lankford, Jr.
*Assistant Examiner*—Christopher R. Tate
*Attorney, Agent, or Firm*—Evans & Burrell; Susan B. Evans

[57] ABSTRACT

The present invention relates to a natural herbal composition of effective amounts of Aloe Vera, Capsicum, Golden Seal, Comfrey Root and water, to its method of use for external application to affected parts of the body for eliminating muscular pain and to its method of preparation.

4 Claims, No Drawings

EXTERNAL HERBAL COMPOSITION FOR TREATING MUSCLE ACHES AND JOINT PAIN

BACKGROUND

The present invention is directed to an herbal composition which has been found to have healing properties, when used on the human body to eliminate muscular aches and pains. The active ingredients are all natural herbs and include Aloe vera, *Symphytum officinale* (common name, Comfrey Root), *Hydrastis canadenis* (Golden Seal), and *Capsicum annuum* (Cayenne pepper). The present invention is applied externally as a poultice or a liquid herbal soak.

Compositions containing Aloe vera, capsicum extract and comfrey extract have been used as a cosmetic composition in combination with other herbal and chemical ingredients (Mausner, U.S. Pat. No. 5,215,759).

Certain of the active ingredients have been used as an ingestible dietary supplement (Emanuel-King, U.S. Pat. No. 5,248,503).

None of this prior art discloses the instant invention.

SUMMARY OF THE INVENTION

The present invention provides a natural herbal composition for external application comprising effective amounts of Aloe Vera, Capsicum, Golden Seal, Comfrey Root (bark-external use only) and water.

The present invention further provides a method for the application of a natural herbal composition suitably formulated for external application to a human body for relief of muscular aches and pains comprising formulating a composition of effective amounts of Aloe Vera, Capsicum, Golden Seal, Comfrey Root (bark-external use only) and water, and applying the composition externally to the body.

The present invention also discloses a process for the preparation of a natural herbal composition formulated as a poultice or liquid herbal soak suitable for external application to the human body for reducing muscular aches and pains comprising:

a). mixing an effective amount of Aloe Vera, Capsicum, Golden Seal, Comfrey Root (bark-external use only) and water;

b). applying heat until said mixture boils;

c). reducing heat to a simmer; and d). continuing to mix until a suitable consistency is formed.

DETAILED DESCRIPTION OF THE INVENTION

The compositions of the present invention are natural herbal compositions for external application to mammals, preferably human beings, particularly the limbs and joints, such as the elbow, knee, back, neck or any joint or muscle mass. The composition of the present invention is used for the purpose of eliminating muscular and joint pain.

The active ingredients utilized in the present invention include Aloe Vera, Capsicum, Golden Seal, Comfrey Root. All of these active ingredients are readily available in herb stores and through herb distributors such as Frontier Herbs, Norway, Iowa 52318.

Aloe Vera (Aloe vera) is also known as Cape, Barbados, Curaiao, Socotrine, or Zanzibaraloe. The part used is the jelly like gel found in the leaves, and the bitter, yellow juice (latex) extracted from specialized cells of the leaves' inner skin. It is known as a prescription to help soothe wounds, burns, scalds and sunburn, and to help avoid infection. Some people experience an allergic reaction when applied as a cosmetic.

Capsicum (*Capsicum annuum*) is also known as hot pepper, cayenne chili pepper and Louisiana long pepper. The part used is the fruit. Capsicum is well known as a digestive aid it is also believed to help cut cholesterol and help treat pain.

Goldenseal (*Hydrastsi canadenis*) is also known as Yellow root, yellow puccoon, Indian turmeric, Indian dye, Indian paint, jaundice root, eye balm, eye root, and golden root. The parts used are the rhizome and roots. Goldenseal is well known in the art as a possible antibiotic or immune system stimulant, or to help ease menstrual flow, take it as an infusion or tincture.

Comfrey Root (*Symphytum officinale*) is also known as Bruisewort, knitbone, boneset or healing herb. The parts used are the bark, roots and leaves. It is well known for its healing and mending effects on wounds and sores. Comfrey has been found to contain certain chemicals (pyrrolizidines) that in large amounts cause serious liver damage and cancer in laboratory animals. Authorities are divided on comfrey's safety for internal use. The instant invention is directed to an external use.

The preferred effective amounts of the active ingredients are: Aloe Vera(liquid) 20–30%, preferably 75% pure Aloe vera juice; Capsicum (powder)10–20%; Golden Seal (powder) 10–20%; and Comfrey Root (bark-external use only) (finely chopped pieces) 40–60%. More preferably Aloe vera 20%; Capsicum (powder)15%; Golden Seal (powder) 15%; Comfrey Root (bark-external use only) (powder) 50%.

The active ingredients of the present invention may be utilized as powders or extracted as tinctures in ethyl alcohol or in oil. The exception is Aloe vera which is utilized as a gel or juice.

An effective amount of water is adjusted according to whether a poultice or a liquid herbal soak is being prepared. When the composition of the present invention is utilized as a soak the amount of water is increased accordingly.

The composition of this invention is specifically directed to an external application. The composition is applied as a poultice or a liquid herbal soak or bath.

A poultice is a composition formulated to have a pasty consistency used to cover the affected area by spreading on a cloth and applying to the affected area or applying directly to the affected area.

A liquid herbal soak is a composition formulated to have a watery consistency and sufficient active ingredient to treat the affected area.

The method for the application of the composition of the present invention is suitably formulated for external application to a human body for relief of muscular aches and pain comprising formulating a composition of effective amounts of Aloe Vera, Capsicum, Golden Seal, Comfrey Root and water, and applying the said composition externally to the body.

When formulated as a poultice the composition is preferably applied by placing said composition on or in a flexible, porous material, wherein that flexible, porous material is selected from a group consisting of natural materials and synthetic materials; preferably natural materials such as cotton, preferably cheesecloth or netting, which is commonly available in fabric or arts and craft stores. Synthetic materials such as any of the many new plastics are also utilized.

The flexible, porous material is preferably formulated as a pouch like carrier in which the composition may be placed. The pouch like carrier may be simple in nature and formed by folding a piece of material over itself and closing off the ends by any suitable means.

The method of applying the composition to the affected area of the body is preferably effected with a heating source, wherein the heating source is selected from the group consisting of heating pad and warm compress, preferably heating pad.

When formulated as a liquid herbal soak the composition is applied by placing the affected body part in a watery solution of the composition, preferably wherein the watery solution of the composition has been heated to a suitably warm temperature, preferably between 70° C. Temp and 90° C. Temp.

The natural herbal composition is prepared by the following process:
 a). mixing an effective amount of Aloe Vera, Capsicum, Golden Seal, Comfrey Root (bark-external use only) and water;
 b). applying heat until said mixture boils;
 c). reducing heat to a simmer; and
 d). continuing to mix until a desired consistency is formed.

A process as described above wherein the preferred effective amounts of the active ingredients are as follows: Aloe Vera(liquid) 20–30%, preferably 75% pure Aloe vera juice; Capsicum (powder)10–20%; Golden Seal(powder) 10–20%; and Comfrey Root (bark-external use only) (finely chopped pieces) 40–60%. More preferably Aloe vera 20%; Capsicum (powder)15%; Golden Seal(powder) 15%; Comfrey Root (bark-external use only) (finely chopped pieces) 50%. Higher or lower levels of active ingredients can, of course be present depending on the intended formulation. Further the active ingredients may be in other forms including liquid extracts of the Capsicum, Golden Seal, and Comfrey Root (bark-external use only).

An example of a poultice formulation

Mix the following active ingredients with 180 ml (¾ c) of water:
 120 ml (½ c) Comfrey Root (bark-external use only) (finely chopped pieces)
 15 ml (1 T) Golden Seal (ground powder)
 15 ml (1 T) Capsicum (ground powder)
 22.5 ml (1½ T) Aloe Vera (juice)
 apply heat at about 100° C. until said mixture boils;
 reduce heat to a simmer and continue to mix until a pasty consistency is formed.

An example of a liquid herbal soak formulation

Mix the following active ingredients with 180 ml (¾ c) of water
 120 ml (½ c) Comfrey Root (bark-external use only) (finely chopped pieces)
 15 ml (1 T) Golden Seal (ground powder)
 15 ml (1 T) Capsicum (ground powder)
 22.5 ml (1½ T) Aloe Vera (juice)
 apply heat at about 100° C. until said mixture boils;
 reduce heat to a simmer; dilute with a suitable amount of warm water for soaking the affected area.

Changes and modifications in the specifically described embodiments can be carried out without departing from the scope of the invention which is intended to be limited only by the scope of the appended claims.

What is claimed is:

1. A natural herbal composition for external application to relieve muscle aches and joint pain comprising water and a mixture of herbal ingredients which have been mixed and boiled therein, wherein the herbal ingredients comprise, by volume:
 liquid Aloe vera, 20–30%;
 powdered golden seal, 10–20%;
 powdered capsicum, 10–20%, and
 finely chopped bark of comfrey root, 40–60%.

2. The natural herbal composition according to claim 1 wherein the external application is in a form selected from the group consisting of poultice and liquid herbal soak.

3. The natural herbal composition according to claim 2 wherein the application is in the form of a poultice.

4. The natural herbal composition according to claim 1 wherein said herbal ingredients comprise, by volume:
 liquid Aloe vera, 20%;
 powdered golden seal, 15%;
 powdered capsicum, 15%, and finely chopped bark of comfrey root, 50%.

* * * * *